United States Patent [19]

Alfs et al.

[11] 4,168,390

[45] Sep. 18, 1979

[54] PROCESS FOR CONTINUOUS ALKYLATION OF PHENOL USING ION EXCHANGE RESINS

[75] Inventors: Helmut Alfs; Heinz Steiner; Karl-Heinz Grünheit; Georg Böhm, all of Marl, Fed. Rep. of Germany

[73] Assignee: Chemische Werke Hüls A.G., Marl, Fed. Rep. of Germany

[21] Appl. No.: 711,461

[22] Filed: Aug. 4, 1976

Related U.S. Application Data

[63] Continuation-in-part of Ser. No. 498,401, Aug. 19, 1974, abandoned.

[30] Foreign Application Priority Data

Sep. 14, 1973 [DE]  Fed. Rep. of Germany ....... 2346273

[51] Int. Cl.² ............................................ C07C 39/06
[52] U.S. Cl. .................................................. 568/793
[58] Field of Search ............... 260/624, 624 C, 624 R; 498/401; 568/790, 780

[56] References Cited

U.S. PATENT DOCUMENTS 3,422,157   1/1969   Kaufman ..................... 260/624 C

FOREIGN PATENT DOCUMENTS 692355   8/1964   Canada ............................... 260/624 C
953929   4/1964   United Kingdom ................ 260/624 C Primary Examiner—James O. Thomas, Jr.
Assistant Examiner—Werren B. Lone
Attorney, Agent, or Firm—Gilbert L. Wells

[57] ABSTRACT

An improved process for the continuous alkylation of phenol with olefins having 6 to 12 carbon atoms in the liquid phase and in the presence of strongly acid ion exchange resin catalysts mounted in a fixed bed. The phenol and olefins are passed in a first stage at temperatures from about 80° to 120° C. over an ion exchange resin catalyst having an exchange capacity of from 50 to 96 m Val per 100 ml of catalyst and then passed in a second stage at temperatures about 110° to 130° C. over another ion exchange resin catalyst having an exchange capacity of from 100 to 180 m Val per 100 ml of catalyst.

5 Claims, No Drawings

PROCESS FOR CONTINUOUS ALKYLATION OF PHENOL USING ION EXCHANGE RESINS

CROSS REFERENCES TO RELATED APPLICATIONS

The present invention is a continuation-in-part of application Ser. No. 498,401, filed Aug. 19, 1974 and now abandoned.

Applicants claim priority under 35 U.S.C. 119 for Application P 23 46 273.9, filed Sept. 14, 1973 in the Patent Office of the Federal Republic of Germany. The priority document is filed in application Ser. No. 498,401.

BACKGROUND OF THE INVENTION

The field of the invention is alkylation of arylhydroxides and the present invention is particularly concerned with a process for preparing alkyl phenols from phenol and olefins having 6 to 12 carbon atoms in the liquid phase and in the presence of strongly acid ion exchange resins mounted in a fixed bed.

The state of the art of the alkylation of phenols and ion exchange resins useful therein may be ascertained by reference to the Kirk-Othmer "Encyclopedia of Chemical Technology", Vol. 1 (1963), pages 894–895, under the section entitled "Alkylation of Phenols": Vol. II (1967), pages 871–899, under the section entitled "Ion Exchange", particularly pages 881 and 882 where capacity is disclosed: U.S. Pat. No. 3,422,157 of Kaufman et al which issued Jan. 14, 1969: U.S. Pat. No. 2,865,966 of Abadir; and U.S. Pat. No. 2,732,408 of Foote; the disclosures of which are incorporated herein.

Kirk-Othmer, Vol. 1 discloses at pages 894 - 895 that olefins in the $C_8$ to $C_{15}$ range do not enter into the alkylation of phenol as readily as the lower olefins, and for maximum efficiency a closer control over catalyst and operating conditions is required. The alkylation can be catalyzed by a sulfonic acid resin at 70°–100° C. or by p-toluenesulfonic acid hydrate at 80°–150° C., or by a Superfiltrol clay at 80° C.

U.S. Pat. No. 3,422,157 of Kaufman et al defines in Claim 1 which is incorporated herein, a continuous process for the alkylation of phenols comprising the steps of (a) maintaining in a continuously recirculating reaction stream, a solvent-free liquefied mixture consisting essentially of phenol and a liquefied olefin having from 4 to 12 carbon atoms and a melting point of less than 150° C., at a temperature between 50° C. and 125° C., and in a molar ratio of from 0.5 to 10 moles of phenol per mole of olefin, (b) passing said mixture through a first reaction zone containing a stationary mass of substantially anhydrous cation exchanging resin containing strongly acidic exchanging groups in acid form and having a large surface, thereby alkylating only a portion of the phenol with at least a portion of said olefin, (c) and passing the resulting reaction mixture through a cooling zone to remove sufficient heat of reaction to keep the reaction temperature below 150° C., (d) continuously feeding to said recirculating stream fresh phenol and olefin reactants in amounts such that the recirculation rate is from 2 to 50 times the reactants feed rate;

(e) continuously withdrawing from said recirculating stream a portion thereof containing the alkylated phenol, said withdrawn portion being substantially equivalent to the volume of the feed, and (f) passing said withdrawn portion directly to a second reaction zone comprising a stationary mass of substantially anhydrous cation exchanging resin containing strongly acidic exchanging groups in acid form and having a large surface area while maintaining sufficient residence time in said second reaction zone to further react and convert the reaction stream to a higher concentration of the desired alkyl phenol;

(g) distilling the effluent from said second reaction zone to remove unreacted phenol and reaction by-product isomers therefrom;

(h) passing the reaction by-product isomers back to the reaction mass between said first and second reaction zones.

It is known to the prior art to alkylate phenol with olefins in the presence of acids, for instance Lewis acids such as sulfuric acid or boron trifluoride. The use of such catalysts requires for instance corrosion-proof equipment, and furthermore, the products obtained lack both the required purity and the desired quality of color.

Attempts have been undertaken to remedy these drawbacks by using activating clays, for instance montmorillonite, as catalysts as disclosed in U.S. Pat. No. 2,732,408. Mostly these catalysts are used in discontinuous operation in stirred vessels. Because of marked contact abrasion, these products however must be separated by means of centrifuges or filter presses from the elutriated catalyst particles. Furthermore, the dwell times are very long and hence lead to low space time yields. Also, even after separating the elutriated catalysts, there remains a tendency toward undesired colorations during further processing.

Recently, strongly acid ion exchange resins in H-ion form, especially sulfonated ion exchange resins such as sulfonated ion exchange resins based on phenol-formaldehyde resins or polystyrene resins or the same have been used as fixed bed catalysts for alkylating, as disclosed in U.S. Pat. No. 3,422,157, and as sold by Bayer AG as Lewatit (R), SC 102 H, SC 104H, SC 108H, SPC 108H and SPC 118H. While high space time yields are obtained, local overheating due to the strongly exothermic reaction may not be reliably excluded. This results in contaminated and especially in discolored alkyl phenols which are unsuitable for further use. Also, the ion exchange resins suffer damage.

The process of U.S. Pat. No. 3,422,157 avoids local overheating by circulating the reaction mixture consisting of the alkyl phenols formed from olefins and phenols via a heat exchanger and through the reactor and by only partly alkylating, whereupon the amount corresponding to the fresh supply of olefins and phenols is subtracted and made to react in a second stage. The drawback of this process consists in the expenditure of circulating the reaction components and in their thermal loading, which leads to dissociation or discoloration of the end products.

SUMMARY OF THE INVENTION

The present invention addresses the problem of alkylating phenol in as simple a manner as possible, and with the least damage, concurrently with high space time yields, into flawless alkylphenols.

The problem faced by the present invention is solved by passing phenol and olefins at temperatures from about 80° to 120° C. in a first stage over a catalyst of an exchange capacity of about 50 to 95 mVal per 100 ml of catalyst and then through a second stage at temperatures from about 110° to 130° C. over a catalyst with an exchange capacity of about 100 to 180 mVal per 100 ml of catalyst.

By mVal is meant the ion-exchange capacity in milliequivalents per 100 ml of catalyst measured in water-wet state as disclosed for example in K. Dorfner "Ionenaustauscherharze" (1970) p. 47.

Olefins used in accordance with the invention contain from 6 to 12 carbon atoms. Generally, the alkylation reaction was carried out at atmospheric pressure. Generally a mole ratio of phenol/olefin = 3/1 is used, preferably 1 1/2/1. When dealing with stoichiometric amounts, which is feasible, undesirably high proportions of dialkyl phenols however are obtained.

Sulfonated ion exchange resins in H-ion form, for instance polystyrene-based or those based on phenol-formaldehyde resins, mounted in a fixed bed, are used as catalysts.

In order to prevent local overheating, the invention provides a catalyst with an exchange capacity of about 50 to 95 mVal per 100 ml of catalyst in the first stage, said exchange capacity reflecting the equivalents of H-ions per 100 ml of ion exchange resins measured in the water-wet state, this capacity preferably being about 70 to 80 mVal per 100 ml of catalyst, and, in the second stage, a catalyst with an exchange capacity of about 100 to 180 mVal per 100 ml of catalyst, preferably about 120 to 140 mVal per 100 ml of catalyst.

Specific examples of ion exchange resin catalyst having a water-wet exchange capacity of about 50 to 95 mVal per 100 ml of catalyst include sulfonated phenol-formaldehyde resins or sulfonated polystyrene resins cross-linked with divinylbenzene or its derivatives which are deactivated for example with $Al_2(SO_4)_3$ or catalysts in the specific examples according to this invention.

Examples of these catalysts are Lewatit (R) products manufactured by Bayer AG, Leverkusen, W. Germany, designated SC 104H with a total capacity of 70-80 mVal per 100 ml and SC 104H with a total capacity of 120 to 130 mVal per 100 ml but reduced to 50 to 95 mVal per 100 ml with $Al_2(SO_4)_3$.

Specific examples of ion exchange resin catalysts having a water-wet exchange capacity of about 100 to 180 mVal per 100 ml of catalyst include Lewatit (R) SC 104H
Lewatit (R) SPC 108H and
Lewatit(R) SPC 118H.

The apparatus useful in the present invention differs from the apparatus shown in FIG. 2 of U.S. Pat. No. 3,422,157 in that the phenol and olefins are passed directly into the two reactors whereby no side stream is drawn off.

DESCRIPTION OF THE PREFERRED EMBODIMENTS

As a rule the initial substances are preheated to about 60°-100° C. by means of a heat exchanger. When the initial substances so pre-heated are made to pass over the catalyst, then the reaction mixture is raised to temperatures of 100° to 120° C. The product flow issuing from the reactor is cooled to about 100° to 105° C. by means of a second heat exchanger. The reaction mixture is raised to a temperature of about 110°-130° C. in the second reactor. Color quality is noticeably degraded at higher temperatures.

In order to obtain a desired deactivation of the catalyst of the first stage prior to operation, the ion exchange resins are treated with aqueous solutions of salt such as aluminum sulfate and dried. Catalyst activity decreases at appreciable length of treatment. When the exchange capacity of the ion exchange resins of the second stage drops below 100 mVal per 100 ml of catalyst, phenols and olefins are made to pass over this catalyst of the original second stage and then over the fresh catalyst with an exchange capacity of 100 to 160 mVal per 100 ml of catalyst, the latter catalyst being exchanged, of the original first stage.

The crude product obtained from every reaction subsequently, and without any kind of pre-treatment, is salvaged by distillation, the non-converted phenol and the olefin again being fed to the reaction mixture. The dialkyl phenol remaining in the sump during distillation is transmitted again into the reaction zone so that conversion into monoalkylphenol takes place.

The alkyl phenols obtained are approximately 99 percent pure, their dye number or color coefficient being about 10 to 20 APHA, according to ASTM D 1209-54.

The process of the invention allows surprising simplicity in preparing alkyl phenols of high yields, while maintaining high space time outputs and very good quality of color.

The example described below explains the process of the invention, without thereby limiting it.

EXAMPLE 1.7 tons of nonene and 2.2 tons of phenol are heated to 70° C. by means of a heat exchanger and are supplied within one hour to a first reactor. The latter is filled with 120 kg of sulfonated polystyrene ion exchange resin Lewatit (R) SC 102H or SC104 deactivated with $Al_2(SO_4)_3$ as manufactured by Bayer AG, Leverkusen, Bayerwerke, W. Germany, with an activity of approximately 80 mVal per 100 ml of catalyst. The reactor diameter is 30 cm and its height is 300 cm. The exhaust temperature at the first reactor is about 120° C. The reaction mixture is cooled to about 100° C. by means of a heat exchanger and supplied to a secnd reactor, which is filled with 120 kg of ion exchange resin Lewatit (R) SC104H with an activity of 140 mVal/per 100 ml of catalyst. In the second reactor, the reaction mixture rises in temperature to approximately 125° C. Taking contact-filling into account, the entire dwell time is about 4 minutes.

| Output in % by weight | stage I | Stage II |
|---|---|---|
| Nonene | 28.9 | 3.8 |
| phenol | 46.1 | 27.5 |
| nonylphenol | 22.4 | 65.8 |
| dinonylphenol | 2.6 | 2.9 |

Following distillation recovery and recycling of the dinonylphenol formed and of the non-converted nonene and phenol, the yield in nonylphenol is 99 percent; the color coefficient or dye number of the nonylphenol is 10 APHA.

The volume of nonene and phenol per hour can be varied between 0.1 to 4.5 tons of nonene and phenol at a mole ratio of phenol/nonene of 1 1/2/1 with comparable results.

Although the specific example uses nonene, comparable results are obtained with any of the olefins having 6 to 12 carbon atoms.

We claim:

1. In a method for preparing monoalkylated phenol from phenol and olefins having 6 to 12 carbon atoms, in the liquid phase and in the presence of strongly acid ion exchange resin catalyst mounted in a fixed bed, the improvement comprising:

passing said phenol and said olefins in a first stage at temperatures from about 80° to 120° C. over said catalyst having an exchange capacity from about 50 to 95 mVal per 100 ml of catalyst and then in a second stage passing said phenol and said olefins at temperatures from about 110° to 130° C. over a catalyst having an exchange capacity from about 100 to 180 mVal per 100 ml of catalyst.

2. The method as defined in claim 1, wherein said phenol and said olefins are passed over said catalyst having an exchange capacity from about 70 to 80 mVal per 100 ml of catalyst in said first stage in a molar ratio of phenol to olefins of 3 to 1, and over said catalyst having an exchange capacity of about 120 to 140 mVal per 100 ml of catalyst in said second stage.

3. The method as defined in claim 1, wherein, following a drop in activity of said catalyst in said second stage to below 100 mVal per 100 ml of catalyst, said phenol and said olefins are passed over said second stage catalyst, said first stage catalyst is exchanged to an exchange capacity from about 100 to 180 mVal per 100 ml of catalyst, and said phenol and said olefins are passed over said exchanged first stage catalyst.

4. In the continuous process for the monoalkylation of phenol comprising the steps of:

(a) maintaining in a continuous reaction stream, a solvent free liquefied mixture consisting essentially of phenol and a liquefied olefin having from 6 to 12 carbon atoms and in a molar ratio of from 0.5 to 10 moles of phenol per mole of olefin;

(b) passing said mixture through a first reaction zone containing a first stationary mass of substantially anhydrous cation exchanging resin containing strongly acidic exchanging groups in acid form and having a large surface thereby alkylating only a portion of the phenol with at least a portion of said olefin;

(c) continuously feeding to said reaction stream fresh phenol and olefin reactants;

(d) continuously withdrawing from said reaction stream the alkylated phenol;

(e) passing said withdrawn alkylated phenol directly to a second reaction zone comprising a second stationary mass of substantially anhydrous cation exchanging resin containing strongly acidic exchanging groups in acid form and having a large surface area while maintaining sufficient residence time in said second reaction zone to further react and convert the reaction stream to a higher concentration of the desired alkyl phenol; and (f) distilling the effluent from said second reaction zone to remove unreacted phenol and reaction by-product isomers therefrom; the improvement comprising:

passing said phenol and said olefins to said first reaction zone at temperatures from about 80° to 120° C. over said first stationary mass having an exchange capacity from about 50 to 95 mVal per 100 ml of stationary mass and passing said withdrawn alkylated phenol to said second reaction zone at temperatures from about 110° to 130° C. over said second stationary mass having an exchange capacity from about 100 to 180 mVal per 100 ml of stationary mass.

5. The process of claim 4, wherein said first stationary mass has an exchange capacity from about 70 to 80 mVal per 100 ml and said second stationary mass has an exchange capacity from about 120 to 140 mVal per 100 ml and said molar ratio is 3 to 1.

* * * * *